United States Patent [19]

Ichikawa et al.

[11] 3,975,454

[45] Aug. 17, 1976

[54] CATALYST FOR HYDRODEALKYLATION OF ALKYLAROMATIC COMPOUNDS AND A PROCESS FOR PRODUCING THE CATALYST

[75] Inventors: Masaru Ichikawa, Tokorozawa; Eiji Tanaka, Kurashiki; Kenzi Tamaru, Kamakura, all of Japan

[73] Assignee: Sagami Chemical Research Center, Tokyo, Japan

[22] Filed: Dec. 5, 1974

[21] Appl. No.: 529,930

Related U.S. Application Data

[62] Division of Ser. No. 295,907, Feb. 22, 1972, abandoned.

[30] Foreign Application Priority Data

Oct. 11, 1971 Japan................................ 46-79425

[52] U.S. Cl.............................. 260/672 R; 208/112
[51] Int. Cl.².......................................... C07C 3/58
[58] Field of Search................... 260/672 R; 208/112

[56] References Cited
UNITED STATES PATENTS

| | | |
|---|---|---|
| 2,414,118 | 1/1947 | Orchin................................. 260/672 |
| 2,577,788 | 12/1951 | McAteer et al...................... 260/672 |
| 3,102,151 | 8/1963 | Haldeman et al.................... 260/672 |
| 3,160,670 | 12/1964 | Foster............................. 260/671 C |
| 3,715,303 | 2/1973 | Wennerberg et al................. 208/112 |
| 3,751,505 | 8/1973 | Bergomi.............................. 260/672 |
| 3,812,028 | 5/1974 | Wennerberg et al................. 208/112 |

Primary Examiner—Delbert E. Gantz
Assistant Examiner—C. E. Spresser
Attorney, Agent, or Firm—Flynn & Frishauf

[57] ABSTRACT

A novel catalyst for hydrodealkylation of alkylaromatic compounds and a process for producing the catalyst are described. The catalyst comprises the compounds formed from either (a) graphite and (b) an alkali metal or (a) graphite, (b) an alkali metal and (c) at least one compound of a metal selected from the group consisting of Group VIII of the Periodic Table. The catalyst of this invention is capable of selectively producing $Ar-C_{n-1}H_{2n-1}$ from $Ar-C_nH_{2n+1}$, wherein Ar is an aromatic radical.

9 Claims, No Drawings

CATALYST FOR HYDRODEALKYLATION OF ALKYLAROMATIC COMPOUNDS AND A PROCESS FOR PRODUCING THE CATALYST

This is a division of application Ser. No. 295,907, filed Feb. 22, 1972, now abandoned.

RELATED APPLICATIONS

This application is related to applications Ser. No. 180,187, filed Sept. 13, 1971, now U.S. Pat. No. 3,830,753; Ser. No. 185,370, filed Sept. 30, 1971 and succeeded by Ser. No. 332,575, filed Feb. 15, 1973, now U.S. Pat. No. 3,842,113; and Ser. No. 184,907, filed Sept. 29, 1971, and succeeded by Ser. No. 333,720, filed Feb. 20, 1973, now U.S. Pat. No. 3,842,121.

BACKGROUND OF THE INVENTION

The present invention relates to a catalyst for effecting hydrodealkylation of alkylaromatic compounds and a process for producing the catalyst. More particularly, this invention relates to a catalyst for hydrodealkylation of alkylaromatic compounds comprising the complex compounds formed from either (a) graphite and (b) an alkali metal or (a) graphite, (b) an alkali metal and (c) at least one compound of a metal selected from the group consisting of Group VIII of the Periodic Table. According to effecting the use of the catalyst of this invention, $Ar\text{-}C_{n-1}H_{2n-1}$ may be selectively produced from $Ar\text{-}C_nH_{2n+1}$, wherein Ar is an aromatic radical.

DESCRIPTION OF THE PRIOR ART

Conventional commercial process for the disproportionation of alkyl benzene and for the reforming of oily distillated components obtained from hydrocracking of terminal alkyl group have been produced by use of various usual reforming catalysts, hydrocracking catalysts which contain, as the main ingredients, the transition metals oxides such as chromia and nickel oxide, or according to the pyrolysis carried out at a high temperature and under high pressure steam; such pyrolysis has been developed only recently.

However, these catalysts do not effect selective cracking at a desirable portion of alkyl moiety, and involves simultaneously hydrocracking of a benzene nucleus. Further, due to the adhesion of the carbonaceous material onto the surface of these catalysts and also due to a sensitive inhibition caused by carbon monoxide, sulfur compounds and the like, the life of the catalysts turns out to be extremely short. Furthermore, according to the method of effecting a hot steam, there lies a great difficulty performing it from chemical viewpoint, in that it requires high pressure (300 atm ~ 1000 atm) and high temperature (500°C ~ 800°C). As a result, much attention should be paid to select the material of apparatus.

BRIEF SUMMARY OF THE INVENTION

It is an object of this invention to provide a novel catalyst for effecting hydrodealkylation of alkylaromatic compounds.

Another object is to provide a catalyst which can selectively produce $Ar\text{-}C_{n-1}H_{2n-1}$ from $Ar\text{-}C_nH_{2n+1}$, wherein Ar is an aromatic radical.

Another object is to provide a catalyst having a high activity for hydrodealkylation of alkylaromatic compounds.

Another object is to provide a catalyst having a longer life for hydrodealkylation of alkylaromatic compounds.

Another object is to provide a process for producing the catalyst for hydrodealkylation of alkylaromatic compounds.

Other objects and advantages of the present invention will become apparent to those skilled in the art from the following description and disclosure.

DETAILED DESCRIPTION OF THE INVENTION

The catalyst according to the present invention is novel, being entirely different from any one of the conventional catalysts in respect of the composition and of the principle for the catalyst formation.

When the catalyst of the present invention is used for the hydrodealkylation of usual alkylaromatic compounds or distillation materials, any carbon and so forth are hardly deposited on the surface of the catalyst proper, and also the catalyst is possessed of strong resistance to poison from carbon dioxide, carbon monoxide, sulfur compounds such as thiophene and so on. In the catalyst, under the suitable reaction conditions such as the ratio of $H_2$ to an alkylaromatic compound, a reaction temperature, a pressure and a flow rate for hydrodealkylation of alkylaromatic compounds, $Ar\text{-}C_{n-1}H_{2n-1}$ may be selectively produced from $Ar\text{-}C_nH_{2n+1}$. Furthermore, if the catalyst is previously treated with hydrogen, ammonia and by the addition of the alumina powder to the catalyst, the deterioration of reaction activity of said catalyst due to the polymerization of alkylbenzene can be prevented, whereby the catalyst will be capable of exhibiting a high activity, and have a longer life.

The catalyst according to the present invention is "a complex compound", which comprises:

Either (a) graphite and (b) at least one of the alkali metals belonging to Group 1A of the Periodic Table or (a) graphite, (b) at least one of the alkali metals belonging to Group 1A and (c) at least one compound of a metal selected from the group consisting of Group 8 of the Periodic Table.

This "complex compound" comprises alkali metals as electron donors, graphites as an electron acceptor, and can contain at least one of said transition metal compounds. Such transition metal compounds also form interlayer compounds with graphite under suitable reaction conditions. [refer to Prog. Inorg. Chem., 1, 125-205 (1959)] At least one halide, oxide or sulfide may be used as a transitional metal compound, and halides are particularly preferable in view of their being readily prepared for use as the catalyst.

The catalyst according to this invention can be prepared by means of either (1) subjecting a mixture of graphite and an alkali metal to a heat treatment under a reduced pressure, for example, at $10^{-3}$ cm Hg or in an inert gas atmosphere such as He, $N_2$ and Ar, at a temperature of from 150°C to 350°C, or (2) forming a graphite-transition metal interlayer complex compound through subjecting a mixture of graphite and the compound of a transition metal belonging to Group VIII of the Periodic Table to a heat treatment at a temperature of from 250°C to 500°C under a reduced pressure in an inert gas atmosphere, thereafter adding an alkali metal the interlayer complex compounds and heating the resultant product, under a reduced pressure or in an inert gas atmosphere such as argon and nitrogen at a temperature above the melting points of the alkali metals. When the catalyst is prepared as above, the weight ratio of the transition metal compound to graphite is generally about 0.001 – 10 : 1, preferably 0.01 – 0.5 : 1, and the weight ratio of alkali metal to graphite-transition metal interlayer complex compounds is generally about 0.1 – 10 : 1 and preferably 0.5 – 1 : 1. In the catalyst comprising graphite and an alkali metal, the weight ratio of the alkali metal to graphite is 0.1 – 10 : 1, preferably 0.5 – 2 : 1.

Graphite employed for preparation of the catalyst can be obtained by pyrolysis of a carbon-containing material, preferably by pyrolysis of active carbon. Graphite in the degree of graphitization, 100 percent can be, without saying, employed for it, and also, partial graphitic carbonaceous materials above the degree of graphitization, 10 percent can be.

With the use of the catalyst according to this invention, various alkylaromatic compounds can be efficiently conducted to hydrodealkylation. For example, a mixed gas of alkylbenzene and hydrogen was passed through at a flow rate of Sv = about 1,000 – 10,000 per hour at a temperature of from about 250°C – 400°C into a flow type fixed bed reactor packed with the catalyst at a room temperature under an atmospheric pressure or above, whereby alkylbenzene was cracked into benzene, alkylbenzene having less carbon atoms than that of the raw material and methane. In the products according to hydrodealkylation of alkylbenzene, high boiling products were readily condensed and collected into a cooling trap which was installed in the reactor. The yield of the desired products formed according to hydrodealkylation in this invention was less than about 90 percent of the theoretical value.

DESCRIPTION OF PREFERRED EMBODIMENTS

The present invention will be further explained in detail by means of Examples. It should be understood that this invention is, however, in no way limited by the Examples, which are given strictly for the purposes of only illustrating some of the essential mode of this invention. All parts given in the Examples are parts by weight, unless otherwise specifically indicated.

EXAMPLE 1

Graphite produced by graphitization treatment of active carbon, and potassium in which the weight ratio of graphite to potassium as about 2 : 1, were charged into a U-shaped glass flow type fixed bed reactor, and heated at 300°C – 350°C for 20 hours under a reduced pressure to form a golden-colored graphite-potassium ($C_8K$) complex compound, while a deep-blue $C_{24}K$ complex compound was formed by the reduction of 5 parts of graphite with one part of potassium at 350°C. The surface area of thus formed catalyst was measured according to the BET method and found to be about 20 $m^2$ per gram.

A gaseous mixture of ethyl benzene, toluene and hydrogen was circulated at a flow rate of space velocity (SV) = about 760 – 950 per hour at a temperature listed in Table 1 into the reactor packed with the catalyst produced as above with the various size of granular graphite listed in Table 1. Thereafter, the products collected into a Dry-ice-methanol trap were subjected to quantitative analysis through gas chromatography. The results are as shown in Table 1 below. Most of the low boiling vapor not collected in the trap was methane. Furthermore, after ten runs of continuous tests, deterioration of the activity of the catalyst was hardly found that might affect the life of the catalyst.

Table 1

| Catalyst | $H_2$/Ethyl* benzene (Molar Ratio) | Reaction Temp. (°C) | SV ($hr^{-1}$) | Conversion (One-Path) (%) | Product** Composition (Molar %) ⬡ | ⬡-$CH_3$ |
|---|---|---|---|---|---|---|
| $C_8K$*** (14 mesh) | 94/6 | 360 | 950 | 4.3 | 42 | 58 |
| $C_8K$ (4 mesh) | 94/6 | 340 | 760 | 4.0 | 35 | 65 |
| $C_8K$ (14 mesh) | 92/8 | 300 | 770 | 1.2 | 22 | 78 |
| $C_{24}K$ (14 mesh) | 94/6 | 350 | 950 | 5.7 | 38 | 62 |

*A total pressure was one atmospheric pressure
**Vapor phase components were methane and ethane
***Shows granular graphite in mesh employed

EXAMPLE 2

Catalysts which comprise grahite-alkali metals, and graphite-transition metal compounds-alkali metals were prepared according to the procedures below, and were thereafter charged into a U-shaped glass flow type fixed bed reactor, followed by conducting hydrodemethylation of toluene.

Graphite employed for preparation of the catalyst was granular having 4–14 mesh produced by graphitization of an active carbon. The degree of graphitization of the thus formed graphite was measured according to the X-ray spectroscopic analysis, and found to be 30% – 90%.

The two component catalyst was prepared by heating a mixture of various size of granular graphite and alkali metals such as potassium, sodium and so forth under a reduced pressure at a temperature of from 300°C to 350°C.

The three component catalyst comprising graphite-transition metal compound-potassium was prepared by mixing graphite with various transition metal compounds in which the weight ratio of graphite to the transition metal compound was about 1 : 0.1, heating the thus formed mixture under a reduced pressure at 350°C in a sealed tube, and thereafter, adding potassium which the weight ratio of potassium to graphite was approximately equal to each other, to the resulting matter above, and heating and fusing the thus resulting mixture at a temperature of from 300°C to 350°C.

A mixed gas of toluene and hydrogen was circulated at a flow rate of SV = about 1000 hr$^{-1}$ at a temperature listed in Table 2 on the catalyst prepared according to the procedures above. Thereafter, the products collected into a Dry-ice-methanol trap were subjected to quantitative analysis through gas chromatography (Apiezon L column at a temperature of from 80°C to 90°C). The results are as shown in Table 2 below. Most of the low boiling vapor not collected into the trap was methane.

Table 2

| Catalyst (Parts by Weight) | H$_2$/Ethyl benzene (Molar Ratio) | Reaction Temp. (°C) | SV (hr$^{-1}$) | Conversion (One Path) |
|---|---|---|---|---|
| Graphite-K (5-4) (Graphite: 4 mesh) | 91/9 | 350 | 790 | 15.8 |
| Graphite-K (5-5) | 94/6 | 350 | 760 | 3.5 |
|  | 94/6 | 400 | 760 | 12.5 |
| (2-1) |  |  |  |  |

EXAMPLE 3

Catalysts prepared according to the procedure as in Example 2 were charged into the flow type fixed bed reactor, and a gaseous mixture of various alkylbenzene with hydrogen was brought into contact with these catalysts at a flow rate of SV = about 10,000 hr$^{-1}$, liquid hourly space velocity (LHSV) = 1.0, at 400°C under 40 atmospheres. The composition of the oily products collected by condensing thereof into a cooling trap was subjected to analysis through gas chromatography. The results of hydrodealkylation of various alkylbenzene are as shown in Table 3 below.

Table 3

| Catalyst (Parts by Weight) | H$_2$/Alkylbenzene (Molar Ratio) | Pressure (Atm.) | Flow Rate | Reaction Temp. (°C) | Oil Yield (Conversion %) | Product Composition (Molar %) |
|---|---|---|---|---|---|---|
| Graphite-K* C$_n$K (10) | H$_2$/Ethylbenzene =90/10 | 40 | SV= 10,000 hr$^{-1}$ | 400 | 80 (76) | 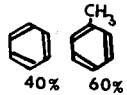 40% 60% |
| C$_n$K (10) | H$_2$/Methylbenzene =95/5 | 40 | LHSV=1.0 | 400 | 90 (86) |  90% |
| C$_n$K (10) | H$_2$/Xylene Mixture =90/10 | 40 | =1.0 | 400 | 60 | 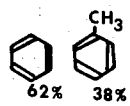 62% 38% |
| C$_n$K (10) | H$_2$/Cumene =90/7 | 40 | =1.0 | 400 | 92 | 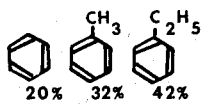 20% 32% 42% |
| Graphite-FeCl$_3$—K (5-1-4) | H$_2$/Ethylbenzene =90/10 | 40 | =1.0 | 400 | 90 | 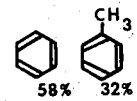 58% 32% |

*The graphite employed was all granular, such as being of 14 mesh produced by graphitization of an active carbon.

| (Graphite: 14 mesh) Graphite-FeCl$_3$—K (5-0.5-3) | 94/7 | 400 | 760 | 17.0 |
|---|---|---|---|---|
| Graphite-NiCl$_2$—K (5-0.5-5) | 94/6 | 400 | 790 | 20.1 |
| Graphite-COCl$_2$—K (5-0.5-5) | 94/7 | 350 | 760 | 9.8 |
| Graphite-RuCl$_3$—K (5-0.5-5) | 94/8 | 400 | 760 | 17.7 |
| Graphite-Na (5-4) | 94/6 | 400 | 770 | 9.2 |
| Graphite-FeCl$_3$—Na (5-1-5) | 94/6 | 400 | 760 | 15.1 |
| Graphite-Rb | 94/6 | 350 | 760 | 4.6 |

EXAMPLE 4

The catalyst prepared according to the procedure in Example 1 was charged into the flow type fixed bed reactor, and hydrodealkylation of n-propylbenzene was carried out in the same operation as in Example 1 under an atmospheric pressure.

The products collected by condensing them into a Dry-ice-methanol trap were subjected to quantitative analysis by means of gas chromatography. The results are as shown in Table 4 below.

Table 4

| *Catalyst | Flow Rate H₂ SV (hr⁻¹) | n-propylbenzene LHSV (hr⁻¹) | Reaction Temp. (°C) | Conversion (%) | Product Composition (Molar %) ⌬ | ⌬-CH₃ | ⌬-CH₂CH₃ |
|---|---|---|---|---|---|---|---|
| C₈K (14 mesh) | 1200 | 0.4 | 400 | 8.1 | 1 | 49 | 50 |
| C₈K (14 mesh) | 1200 | 0.4 | 350 | 4.2 | 2 | 58 | 40 |
| C₈K (14 mesh) | 600 | 0.2 | 400 | 17.1 | 3 | 46 | 51 |
| C₈K (14 mesh) | 2900 | 0.8 | 400 | 6.0 | 3 | 47 | 50 |

*The catalyst comprises 5 grams of graphite and 4 grams of potassium.

EXAMPLE 5

In contact with the catalyst prepared according to the procedure as in Example 1, hydrodealkylation of isopropylbenzene was carried out under an atmospheric pressure. The products collected by condensing them into a Dry-ice-methanol trap were subjected to quantitative analysis by means of gas chromatography. The results are as shown in Table 5 below.

methanol trap were subjected to quantitative analysis by means of gas chromatography. Selectivity is as shown in Table 6. Conversion, 7.1%. Four-mesh graphite was employed.

Table 6

|  | Benzene | Toluene | Ethyl-benzene | Iso-propyl-benzene | Sec-Butyl-benzene |
|---|---|---|---|---|---|
| Selectivity (%) | 3.0 | 1.5 | 25 | 20.6 | 50 |

Table 5

| *Catalyst | Flow Rate H₂ SV (hr⁻¹) | n-propylbenzene LHSV (hr⁻¹) | Reaction Temp. (°C) | Conversion (%) | Product Composition (Molar %) ⌬ | ⌬-CH₃ | ⌬-CH₂CH₃ |
|---|---|---|---|---|---|---|---|
| C K (14 mesh) | 1200 | 0.4 | 400 | 3.7 | 20 | 53 | 27 |
| C K (14 mesh) | 1200 | 0.4 | 350 | 4.6 | 15 | 55 | 30 |
| C K (14 mesh) | 600 | 0.2 | 350 | 4.5 | 33 | 23 | 44 |
| C K (14 mesh) | 600 | 0.2 | 400 | 11.8 | 31 | 27 | 42 |

*The catalyst comprises 5 grams of graphite and 4 grams of potassium.

EXAMPLE 6

Sec-pentylbenzene and hydrogen were circulated at flow rates of sec-pentylbenzene, LHSV = about 0.29 hr⁻¹ and hydrogen, SV = 860 hr⁻¹, respectively at a temperature of 400°C, on the catalyst prepared according to the procedure as in Example 1, and hydrodealkylation of sec-pentylbenzene was carried out. The products collected by condensing them into a Dry-ice-methanol trap were subjected to quantitative analysis by means of gas chromatography. Selectivity is as shown in Table 6. Conversion, 7.1%. Four-mesh graphite was employed.

EXAMPLE 7

Hydrodealkylation of butylbenzenes was carried out on the catalyst prepared according to the procedure as in Example 1. The Products were subjected to quantitative analysis. The results are as shown in Table 7.

Table 7

| Reactant | *Catalyst | Flow Rate H₂ SV (hr⁻¹) | Butyl-benzene LHSV (hr⁻¹) | **Con- Temp. (°C) | Conver-sion (%) | Benzene | Toluene | Product Composition (Molar %) Ethyl-benzene | n-propyl-benzene | iso-propyl-benzene |
|---|---|---|---|---|---|---|---|---|---|---|
| n-Butylbenzene | C₈K 14 mesh | 1200 | 0.4 | 400 | 1.54 | 9.7 | 53.9 | 36.4 | — | — |
| iso-Butylbenzene | C₈K 14 mesh | 1200 | 0.4 | 400 | 6.9 | 2.3 | 76.1 | — | 21.6 | — |
| sec-Butylbenzene | C₈K 14 mesh | 1200 | 0.4 | 400 | 8.8 | 4.3 | 0.7 | 75.5 | — | 19.5 |
| tert-Butylbenzene | C₈K 14 mesh | 1200 | 0.4 | 400 | 1.6 | 33.7 | 44.2 | 22.1 | — | — |
| n-Butylbenzene | C₈K 4 mesh | 600 | 0.2 | 400 | 3.02 | 11.7 | 52.0 | 30.1 | — | — |
| iso-Butylbenzene | C₈K 4 mesh | 600 | 0.2 | 400 | 26.4 | 5.8 | 50.0 | 3.1 | 31.3 | — |
| sec-Butylbenzene | C₈K 4 mesh | 600 | 0.2 | 400 | 22.9 | 5.4 | 3.0 | 68.6 | — | 23.0 |
| tert-Butylbenzene | C₈K 4 mesh | 600 | 0.2 | 400 | 14.0 | 15.8 | 33.6 | 50.6 | — | — |

Table 7-continued

| Reactant | *Catalyst | Flow Rate H₂ SV (hr⁻¹) | Butyl-benzene LHSV (hr⁻¹) | **Con- Temp. (°C) | Conver- sion (%) | Benzene | Toluene | Product Composition (Molar %) Ethyl-benzene | n-propyl-benzene | iso-propyl-benzene |
|---|---|---|---|---|---|---|---|---|---|---|
| Butylbenzene | 4 mesh | | | | | | | | | |

*The catalyst comprises 5 grams of graphite and 4 grams of potassium.

EXAMPLE 8

Hydrodealkylation of various C₉-aromatic hydrocarbons was carried out on the catalyst prepared according to the procedure as in Example 1. The products were subjected to quantitative analysis. The results are as shown in Table 8 below.

Table 8

| Reactant | Catalyst | Flow Rate H₂ SV (hu⁻¹) | R LHSV (hr⁻¹) | Reaction Temp. (°C) | **Con-ver-sion (%) | Composition (Molar %) Benzene | Toluene | Product Ethyl-benzene | o-Xylene | m-Xylene | p-Xylene |
|---|---|---|---|---|---|---|---|---|---|---|---|
| 1,2,3-Tri-methylbenzene | C₈K 14 mesh | 1200 | 0.4 | 400 | 20.1 | 3.2 | 2.6 | — | 48.4 | 42.6 | — |
| 1,2,4-Tri-methylbenzene | C₈K 14 mesh | 1200 | 0.4 | 400 | 14.2 | — | 4.9 | — | 16.0 | 12.5 | 66.7 |
| 1,3,5-Tri-methylbenzene | C₈K 14 mesh | 1200 | 0.4 | 400 | 8.3 | 3.8 | 12.5 | — | — | 8.35 | — |
| o-Ethyl-toluene | C₈K 14 mesh | 1200 | 0.4 | 400 | 3.5 | — | 14.5 | 78.1 | 7.4 | — | — |
| m-Ethyl-toluene | C₈K 14 mesh | 1200 | 0.4 | 400 | 8.2 | 1.7 | 20.9 | 22.0 | — | 55.4 | — |
| p-Ethyl-toluene | C₈K 14 mesh | 1200 | 0.4 | 400 | 5.6 | 0.9 | 13.8 | 26.3 | — | — | 59.0 |
| C₉-Distillation | C₈K 4 mesh | 600 | 0.14 | 400 | | 11.6 | 25.2 | 4.4 | 11.1 | 19.2 | 28.4 |
| C₉-Distillation | *C₈K | 600 | 0.14 | 400 | | 6.1 | 30.1 | 3.7 | 20.2 | 21.0 | 18.9 |

*large pore radius, small surface area
**Mole/Mole (%)

What we claim is:

1. A process for hydrodealkylating an alkylaromatic compound comprising contacting an alkylaromatic compound and hydrogen at a temperature of from about 250°C. to about 400°C., with an electron donor-acceptor complex catalyst comprising (a) graphite and (b) an alkali metal, the weight ratio of the alkali metal to graphite of said catalyst being from 0.1 : 1 to 10 : 1.

2. The process of claim 1, wherein the alkylaromatic compound is an alkylbenzene.

3. The process of claim 1, wherein said catalyst is prepared by subjecting a mixture of (a) and (b) under a reduced pressure or in an inert gas atmosphere at a temperature of from about 150°C. to about 350°C.

4. The process of claim 1, wherein the alkylaromatic compound and hydrogen are so contacted at a flow rate of space velocity of from about 1000 to about 10,000 per hour.

5. The process of claim 1, wherein the catalyst comprises (a) graphite, (b) an alkali metal and (c) a compound of a metal selected from Group VIII of the Periodic Table, and the weight ratio of metal compound to graphite of said catalyst is from about 0.001 : 1 to about 10 : 1.

6. The process of claim 5, wherein the metal compound is a chloride, an oxide or a sulfide.

7. The process of claim 5, wherein the metal compound is a chloride of a metal selected from the group consisting of iron, nickel, cobalt, ruthenium and osmium.

8. The process of claim 5, wherein said catalyst is prepared by
   i. heating a mixture of graphite and said metal compound at a temperature of from about 250°C. to about 500°C. to form a graphite-metal compound interlayer complex,
   ii. adding an alkali metal to the interlayer complex of (i), and
   iii. heating the resulting mixture formed in (ii) under a reduced pressure or in an inert gas atmosphere at a temperature above the melting point of the alkali metal to form said electron donor-acceptor complex.

9. The process of claim 5, wherein the alkylaromatic compound and hydrogen are so contacted at a flow rate of space velocity of from about 1000 to about 10,000 per hour.

* * * * *